(12) United States Patent
Wimberger-Friedl et al.

(10) Patent No.: US 12,198,346 B2
(45) Date of Patent: Jan. 14, 2025

(54) COMBINING pH AND METABOLIC ACTIVITY IMAGING FOR RESPONSE ASSESSMENT IN IMMUNE THERAPY

(71) Applicant: KONINKLIJKE PHILIPS N.V., Eindhoven (NL)

(72) Inventors: Reinhold Wimberger-Friedl, Waalre (NL); Vanda Lucia de Carvalho Vittorino de Almeida, Veldhoven (NL); Ulrich Katscher, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1182 days.

(21) Appl. No.: 16/959,746

(22) PCT Filed: Dec. 28, 2018

(86) PCT No.: PCT/EP2018/097141
§ 371 (c)(1),
(2) Date: Jul. 2, 2020

(87) PCT Pub. No.: WO2019/134896
PCT Pub. Date: Jul. 11, 2019

(65) Prior Publication Data
US 2020/0372653 A1    Nov. 26, 2020

(30) Foreign Application Priority Data
Jan. 4, 2018   (EP) .................... 18150251

(51) Int. Cl.
*G06T 7/00* (2017.01)
*A61B 5/00* (2006.01)
(Continued)

(52) U.S. Cl.
CPC ........... *G06T 7/0016* (2013.01); *A61B 5/055* (2013.01); *A61B 5/4842* (2013.01);
(Continued)

(58) Field of Classification Search
CPC ................. G06T 7/0016; G06T 7/11; G06T 2207/10088; G06T 2207/10104;
(Continued)

(56) References Cited

U.S. PATENT DOCUMENTS

2006/0177378 A1   8/2006   Norfray
2012/0130223 A1*  5/2012   Reicher .................. G16H 30/40
                                                                 600/407
(Continued)

FOREIGN PATENT DOCUMENTS

WO   2015145447 A2   10/2015
WO   WO-2016140974 A1 *  9/2016

OTHER PUBLICATIONS

Longo, et al., "In Vivo Imaging of Tumor Metabolism and Acidosis by Combining PET and MRI-CEST pH Imaging", Cancer Research, vol. 76, No. 22, Nov. 15, 2016, pp. 6463-6470.
(Continued)

*Primary Examiner* — Ashley K Buran
*Assistant Examiner* — Helene Bor (57) ABSTRACT

A computerized system for monitoring cancer therapy and a related method. The system comprises an input port (IN) for receiving two or more input images acquired of a subject, the two or more input images capable of recording metabolic activity and extracellular pH level. An evaluator (EVAL) of the system is configured to assess, based on the input images, i) a change over time in metabolic activity and ii) a change over time in extracellular pH level. The evaluator (EVAL) is further configured to establish, based on the assessment, an indication on whether or not there is a response to a cancer therapy in relation to a lesion of the subject or on whether the assessment is inconclusive. The indication is output through an output interface (OUT).

10 Claims, 2 Drawing Sheets

(51) Int. Cl.
*A61B 5/055* (2006.01)
*A61B 5/145* (2006.01)
*A61B 6/03* (2006.01)
*G06N 20/00* (2019.01)
*G06T 7/11* (2017.01)
*G16H 15/00* (2018.01)
*G16H 20/40* (2018.01)
*G16H 30/40* (2018.01)
*G16H 50/20* (2018.01)
*G16H 50/50* (2018.01)

(52) U.S. Cl.
CPC .......... *A61B 5/4848* (2013.01); *A61B 5/4866* (2013.01); *A61B 6/037* (2013.01); *G06N 20/00* (2019.01); *G06T 7/11* (2017.01); *G16H 15/00* (2018.01); *G16H 20/40* (2018.01); *G16H 30/40* (2018.01); *G16H 50/20* (2018.01); *G16H 50/50* (2018.01); *A61B 5/1451* (2013.01); *A61B 5/14539* (2013.01); *A61B 2576/00* (2013.01); *G06T 2207/10088* (2013.01); *G06T 2207/10104* (2013.01); *G06T 2207/30096* (2013.01)

(58) Field of Classification Search
CPC .......... G06T 2207/30096; G16H 20/40; G16H 50/50; G16H 15/00; G16H 50/20; G16H 30/40; G06N 20/00; A61B 5/055; A61B 5/4842; A61B 5/4848; A61B 5/4866; A61B 6/037; A61B 5/1451; A61B 5/14539; A61B 2576/00
See application file for complete search history.

(56) References Cited

U.S. PATENT DOCUMENTS

2013/0329973 A1* 12/2013 Cao ...................... G06T 7/0016
382/128
2014/0154185 A1* 6/2014 Van Zijl .................... A61B 5/74
424/9.35
2017/0135615 A1* 5/2017 Hasan ................ A61B 5/14551
2019/0374105 A1* 12/2019 Raylman .............. A61B 6/4417

OTHER PUBLICATIONS

Gawlitza, et al., "In vivo Correlation of Glucose Metabolism, Cell Density and Microcirculatory Parameters in Patients with Head and Neck Cancer: Initial Results Using Simultaneous PET/MRI", PLOS One, vol. 10, No. 8, Aug. 13, 2015, pp. 1-12.

Anonymous, "Response evaluation criteria in solid tumors", Wikipedia, Nov. 11, 2017, Retrieved from the Internet: URL:https://en.wi kipedia.org/w/index.php?title=Response_evaluation_criteria_in_ solidtumors&oldid=809754104, 5 pages (Abstract).

Anonymous, "PET response criteria in solid tumors", Wikipedia, Apr. 10, 2016, Retrieved from the Internet: URL:https://en.wikipedia. org/w/i ndex.php?title=PET response criteria in solid tumors&oldid= 714520181, 2 pages (Abstract).

Anonymous: "Standardized uptake value", Wikipedia, Dec. 13, 2017, Retrieved from the Internet: URL:https://en.wi ki pedi a.org/ w/i ndex.php?title=Standardized uptakevalue&oldid=815220289, 4 pages (Abstract).

International Search Report and Written Opinion for International Application No. PCT/EP2018/097141, filed Dec. 28, 2018, 15 pages.

Zhang, et al., "Tumor pH and its measurement", J. Nucl. Med. Aug. 2010; 51(8), pp. 1167-1170.

Kircher, er al., "Molecular imaging for personalized cancer care", Molecular Oncology 6 (2012), pp. 182-195.

Zaimenko, Inna et al "Approaches and Techniques to Characterize Cancer Metabolism in vitro and in vivo", BBA Reviews on Cancer, vol. 1868, 2017, pp. 412-419.

Anemone, Annasofia et al "In vivo Evaluation of Tumour Acidosis for Assessing the Early Metabolic Response and Onset of Resistance to Dichloroactate by using Magnetic Resonance pH Imaging", International Journal of Oncology, vol. 51, 2017, pp. 498-506.

* cited by examiner

COMBINING pH AND METABOLIC ACTIVITY IMAGING FOR RESPONSE ASSESSMENT IN IMMUNE THERAPY

RELATED APPLICATIONS

This application is the U.S. National Phase application under 35 U.S.C. § 371 of International Application No. PCT/EP2018/097141, filed on Dec. 28, 2018, which claims priority to European Application No. 18150251.9, filed Jan. 4, 2018. These applications are hereby incorporated by reference herein.

FIELD OF THE INVENTION

The invention relates to a computerized system for monitoring cancer therapy, to a computer-implemented method for monitoring cancer therapy, to a computer program element, and to a computer readable medium.

BACKGROUND OF THE INVENTION

With the introduction of checkpoint blockade immunotherapies (CBIT), treatments that modulate the immune system, have become an important class of therapy for cancer, with FDA approvals for many cancer types even in first line. These therapies can achieve durable responses in late stage patients. However, the percentage of responders is, depending on the cancer type, only between 15 and 30% for monotherapy. Another characteristic of checkpoint blockade therapy is the late time point where response is becoming evident.

A basic mechanism of CBIT is the activation of cytotoxic T cells which are able to recognize the tumor as foreign. By blocking the checkpoint molecules on the target cells an effector function can be engaged and tumor cells can be killed by the infiltrating T cells. Due to the memory of the primed T cells this response can be durable. However, several mechanisms have been described that lead to resistance to the therapy. See for instance the review of P. Sharma et al, in Cell, vol 168, pp. 707-723, 2017. So far no reliable biomarkers have been identified that can predict the response of a patient. Therefore, early response measurement is of high clinical importance.

SUMMARY OF THE INVENTION

There may therefore be a need for a system and/or method to better cancer therapy monitoring.

The object of the present invention is solved by the subject matter of the independent claims where further embodiments are incorporated in the dependent claims. It should be noted that the following described aspect of the invention equally applies to the method of cancer therapy monitoring, to the computer program element and to the computer readable medium.

According to a first aspect of the invention there is provided a computerized system for monitoring cancer therapy, comprising:

An input port for receiving two or more input images acquired of a subject, the two or more input images capable of recording metabolic activity and extracellular pH level;

an evaluator configured to assess, based on the input images, i) a change over time in metabolic activity and ii) a change over time in extracellular pH level and configured to establish, based on the assessment, an indication on whether or not there is a response to a cancer therapy in relation to a lesion of the subject or on whether the assessment is inconclusive; and an output interface for outputting said indication.

According to one embodiment, the evaluator configured to establish in the indication that there is response to the cancer therapy if i) there is an increase in metabolic activity and there is increase in extracellular pH level or ii) there is a decrease in metabolic activity and increase in extracellular pH level.

According to one embodiment, the evaluator configured to establish in the indication whether the response is a pseudo-progression or a true progression.

According to one embodiment, the evaluator includes an image segmenter to segment the two or more images for a region of interest, "ROI", wherein the assessment of the changes of the metabolic activity and the extracellular pH level is based on image values in said ROI.

According to one embodiment, the assessment of the changes of the metabolic activity and the extracellular pH level is based on image values in a border portion of the ROI.

According to one embodiment, the assessment of the changes of the metabolic activity and the extracellular pH level is based on computing one or more ratios of said changes.

According to one embodiment, the at least one image that records the metabolic activity is based on an PET image (signal) and/or wherein the at least one image that records the pH level is based on MR (magnetic resonance) signals such as an MR image, or is at least derivable from an MR image signal. In other words, the imagery that record the metabolic activity or the pH may have natively a suitable contrast or the intensities as per the imagery may need to be converted or otherwise image processed, such as in PET, where the radioactive intensities as recorded in voxel positions are converted into SUV (standard uptake value), or so called maxSUVs, to better represent a measure for metabolic activity. The MR imaging as used herein should be read broadly to include magnetic resonance spectroscopy.

According to a second aspect there is provided a computer-implemented method to monitor cancer therapy, comprising the steps of:

receiving two or more input images acquired of a subject, the two or more input images capable of recording metabolic activity and extracellular pH level;

assessing, based on the input images, i) a change over time in metabolic activity and ii) a change over time in extracellular pH level;

establishing, based on the assessing, an indication on whether or not there is a response to a cancer therapy in relation to a lesion of the subject or on whether the assessment is inconclusive; and outputting said indication.

According to one embodiment, the establishing includes establishing in the indication that there is response to the cancer therapy, if i) there is an increase in metabolic activity and there is increase in extracellular pH level or ii) there is a decrease in metabolic activity and an increase in extracellular pH level.

According to one embodiment, the established indication is capable of distinguishing between a pseudo-progression and a true progression.

According to one embodiment, the at least one image that records the metabolic activity is based on (eg, is derivable from) a PET image and/or wherein the at least one image that records the extracellular pH level is based on (eg, is derivable from) an MR image. Radiological modalities are advantageous as this modality provides information about lesions with a minimum invasiveness as compared to pathology which would require consecutive biopsies and ideally biopsies from all lesions.

According to one embodiment, the establishing step includes applying machine learning to the images.

According to a third aspect there is provided A computer program element, which, when being executed by at least one processing unit, is adapted to cause the processing unit to perform the method as per any one of the above mentioned aspects or embodiments.

According to a fourth aspect there is provided a computer readable medium having stored thereon the program element.

What is proposed herein is as system and method for improved clinical interpretation of the assessment of a tumor lesion by non-invasive data collection (in particular radiology imaging) using metabolic markers in combination with an extracellular pH change sensitive modality. By analyzing and combining both, the change over time in metabolic activity and change over time in extracellular pH level, it becomes in particular possible to distinguish activity of tumor cells from immune cells activity, to so conclude whether the tumor is progressing, stable or responding or even regressing with the currently administered therapy.

In the proposed system it is also possible to distinguish when the metabolic assessment by radiology is not conclusive and this way securing a correct interpretation of the radiology images.

DEFINITIONS

A "response" to a cancer therapy is either a regression or a pseudo-progression.

A "regression" is a state where cancer cells are dying due to the therapy.

The opposite of a "response" is a none-response which comprises a "progression" (cancer cells proliferate) or the lesion remaining "stable".

A "pseudo-progression" is activity of the lesion that looks or behaves akin a progression but is in fact not progression. This term is of particular relevance in immunotherapy where metabolic activity of immune cells ("T cells") may be mistaken for metabolic activity of the tumor.

An "increase of pH level" as used herein indicates lower acidity, that is a higher numeric reading in the pH scale from 0 to 14. For instance, a reading of, say, "8", is at a higher pH level than, say, "5".

"Tumor" or "(cancer) lesion" are being used interchangeably herein. "Metabolic activity" as used herein includes chemically transforming (or processing) certain chemical compounds ("metabolites") by a cell of the human or animal body. One important but non-limiting example is the transformation of glucose to obtain energy.

"Image" as used herein should be construed broadly, to include not only a whole array of image signals but, in an extreme case, a single image signal for a single voxel position or a selection of such image signals for a sub-set of voxel positions in the whole field of view.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
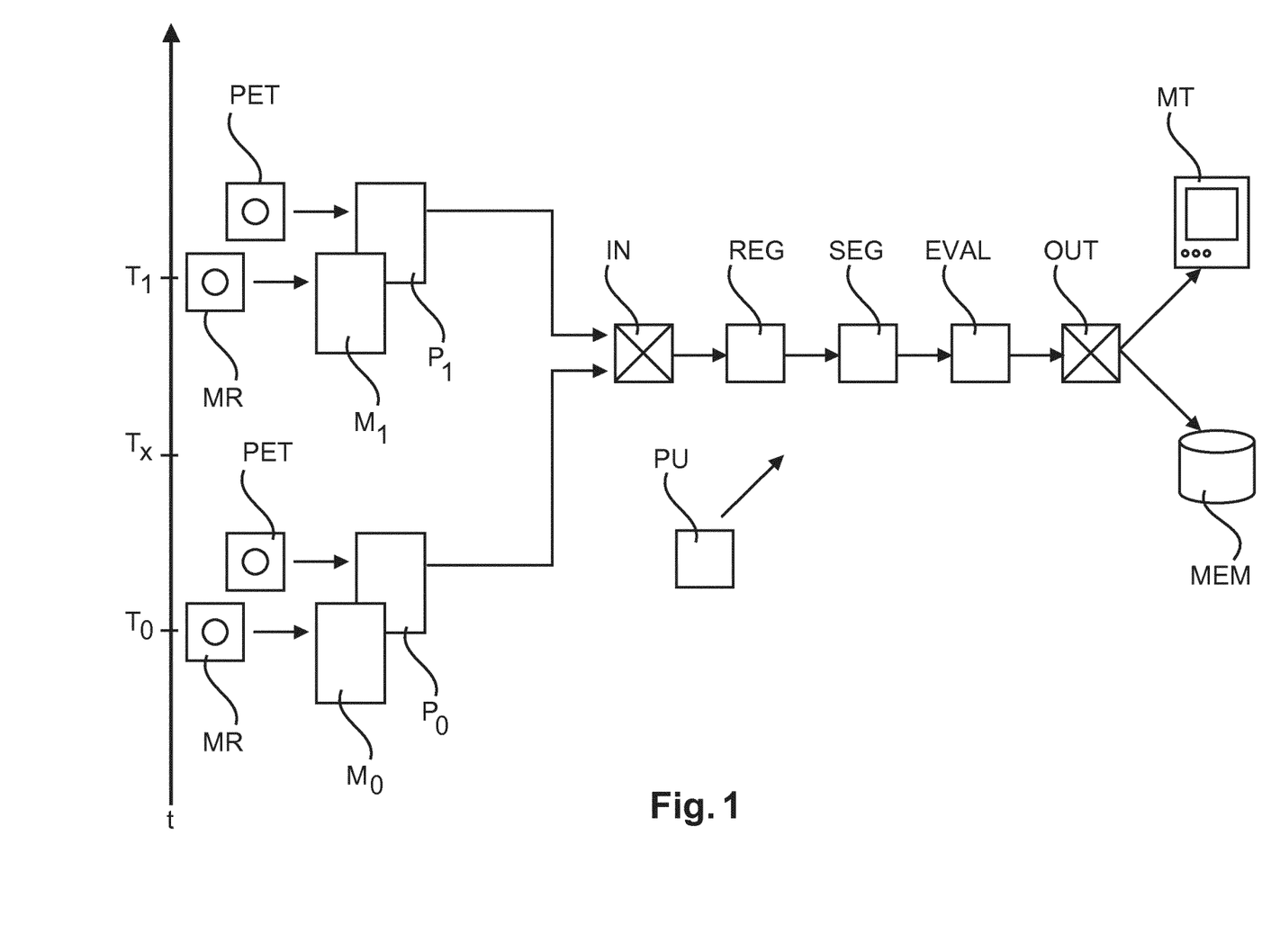
FIG. 1 shows a systematic block diagram of a computerized system for cancer therapy monitoring.

Reference is now made first to the schematic block diagram in FIG. 1 which shows a computerized system to monitor a cancer therapy administered to a subject such as a human or animal patient. In particular, immunotherapy such as CBIT is envisaged herein in a preferred embodiment, but this not at the exclusion of other types of cancer therapy. In other words, although in following immunotherapy is mainly mentioned, the teaching herein is also suitable for other cancer therapies (such as chemotherapy, or targeted therapies or others) and any of these other cancer therapies are specifically envisaged herein in alternative embodiments.

Briefly, the proposed system allows to reliably and early (within weeks rather than months) establish whether the patient responds to the cancer therapy, that is whether the cancerous lesion is regressing, stable, progressing or whether there is so-called pseudo-progression.

In the case of progression, one can then switch early to a different therapy that might be more effective. This is because it has been found as indicated in the background that in a large proportion of cases a patient is not actually responding to immunotherapy, that is, the cancerous lesion is actually proliferating despite immunotherapy being applied.

The proposed computerized immunotherapy monitoring system is run in one embodiment as software on a data processing unit PU such as a computer device, or on multiple computers connected in a network or is implemented in hardware such as a programmed microchip such as a FPGA or on a hardwired chip or other circuitry.

Operation of the system is image based. Specifically, images of the patient are acquired by suitable imaging modalities. The imagery, referred to herein as input imagery, is fed into the system via one or more input ports IN. The input imagery comprises base line imagery IM_0 acquired at time $T_0$ before cancer therapy commences at time $T_X$. The input imagery further comprises a second set of imagery, called control imagery IM_1, and this is acquired later, at $T_1$, after $T_X$. One or more sets of control imagery IM_1 may be acquired after or during administration of the therapy. The same or similar imaging modalities are used for IM_1 as they have been for IM_0.

It has been found by Applicant that the investigation of both, extracellular pH level changes and metabolic activity changes at or around the lesion during the course of treatment provides a highly reliable bio-marker for assessing in particular immunotherapy response or responses to other cancer therapy regimes. It is proposed then herein to measure the changes of both factors, extracellular pH level and metabolic activity, based on suitable imagery that is sensitive to these two factors.

Suitable imaging modalities include in one embodiment MR (magnetic resonance) imaging and PET (positron emission tomography) imaging. More specifically, an MRI imager MRI is used to acquire MR imagery with suitable contrast agents to image for extracellular pH levels. Specifically, in one embodiment for the pH level imaging, CEST-MRI is used. It is advantageous herein to use imaging techniques that are capable of differentiation of extra- from intra-cellular pH. Suitable CEST MRI markers for extracellular pH imaging envisaged herein include appropriate CEST agents, such as 3-aminopropyl phosphonate (3-APP)

or, 2-imidazole-1-yl-3-ethoxycarbonyl propionic acid (IEPA). It has been found that CEST measurement varies not only with pH, but also with CEST agent concentration. However, the confounding concentration factor can be removed by analyzing the relative CEST effect from different exchangeable molecules ("ratiometric CEST").

A specific type of CEST, such as APT imaging "Amide Proton Transfer" is also envisaged herein. Further details on APT may be found in Zhou J, et al., Nat Med. 2003, 9, p 1085.

MR Spectroscopy (MRS) or MR Spectroscopic Imaging (MRSI) is also envisaged to measure pH level. Specifically, intravenous injection of hyperpolarized 13C-labeled bicarbonate results in the rapid production of hyperpolarized 13CO2 in the reaction catalyzed by carbonic anhydrase, which depends on local pH. The ratio of 13C signal intensities from H13CO3 and 13CO2, measured using MRS, can be used to calculate (predominantly) extracellular pH.

An overview of in vivo pH measurement techniques can be found in X. Zheng et al., J Nucl. Med., vol 51(8), pp 1167-1170, August 2010

A PET imager PET is used to image for metabolism activity based on suitable tracers such as FDG (Fluorodeoxyglucose, preferably 18F), but imaging for other compounds than sugar/glucose is also envisaged, such as for lactate. Appropriate tracers envisaged herein for imaging metabolic activity includes $^{18}$F-FDG and $^{64}$Cu-DOTA-pH-LIP amongst others.

The metabolic activity includes chemically processing certain chemical compounds ("metabolites") by cells of the human or animal body. One example is the processing of glucose to obtain energy. This or similar activities can be measured in functional radiological imaging (such as PET or SPECT) by injecting, prior to imaging, radioactive tracers that are similar to metabolites and that are hence "taken up" by the cells for processing as if they were true metabolites (radiolabeling). This gives rise to an image contrast mechanism where high activity corresponds to high radioactive concentrations and hence high image intensities/contrasts. For instance, $^{18}$F-FDG as envisaged herein is a type of glucose which is known (Warburg effect) to be consumed in high quantities by tumors. However, other tracers may be used instead, depending on the metabolic activity or metabolic pathways one wishes to radiolabel and image for.

Sometimes, the image values as per the PET imagery is converted into SUVs (standardized uptake values) for better comparison, where the measured radioactivity is normalized relative to patient weight and originally injected dose of the tracer. "SUVmax", as the maximum value of SUV in a particular ROI lesion is often used in the clinical decision making. Although the mean of the SUV over the ROI may be used instead, the SUVmax is preferred herein as this has been found to be a better estimate of the true SUV than the mean of the SUV. SUV max has also been found to have significantly improved reproducibility. See Paul E Kinahan et al in "PET/CT Standardized Uptake Values (SUVs) in Clinical Practice and Assessing Response to Therapy", Semin Ultrasound CT MR, December 2010 December, vol 31(6), pp 496-505.

The MRI and PET baseline imagery acquired at the time point $T_0$ before commencement of the cancer therapy is designated herein as M0 for the pH level sensitive imagery and "P0" is used as a designation for the metabolism activity sensitivity PET imagery.

At one or more time points T1 after or during the treatment, the control imagery IM_1 is obtained with the MRI and PET imaging modalities and these are indicated herein as M1 and P1 respectively.

In total then, at least four images are acquired although the respective imaging pairs (M0,M1) and (P0,P1) may be fused respectively into single images, in which case the input imagery comprises two images. There may also be imaging modalities that are capable of producing imagery with contrast for both, pH level and metabolism in which case the input imagery also comprises merely two images at any one monitoring instant. In addition to this functional imaging, there may be further imagery (base line and control) for morphological imaging such as through CT or radiography imagery, phase contrast imagery, or Ultrasound (US) imagery or other. In particular the CT morphological information may be used for registration with the MRI images that also have a morphological component with high resolution. So depending on the embodiment, there may be 6 input images, or even more depending on how the MR is analyzed.

After inputting the input imageries comprising the two pairs M0/M1 and P0/P1 into the system at input port IN, a registration module REG is used to voxel-wisely register the respective image pairs onto each other, that is i) M0 onto M1 and P0 onto P1 or ii) M0 onto P0 and M1 onto P1. However, in particular the latter registration is optional if the imagery is natively registered and no specific registration step is required, which may be the case when using a combined PET-MR tandem imager for instance.

The input imagery is then processed by an image segmenter unit SEG to segment the imagery for a portion of the image that includes the region of interest (ROI), in particular the cancerous lesion. Background image information may be cropped out. Use of the segmenter SEG is preferable but not necessary for all embodiments. Alternatively, segmentation is done first and then the registration. Registration can then be focused on the ROI only which is in general easier and consumes less CPU time than whole-body registration.

The input imagery, after optional registration and/or optional segmentation, is then forwarded to an evaluation unit EVAL that is configured to assess as per the input imagery the extracellular pH level change and the metabolism changes at or around the lesion.

The evaluation unit EVAL is further configured to establish based on the assessment of the pH level and metabolic changes, an indication that is indicative on whether the lesion is responding or not or whether the assessment is inconclusive.

The indication may be provided in graphic form and/or in alphanumeric/text form. The indication may be visual or haptic or may be an audio signal or other. The indication, if visual, may be rendered on a display device MT. The indication may be stored in a memory MEM such as a medical database or other or may be otherwise processed.

The indication may be qualified probabilistically, so rather than indicating that the lesion responds, the indication may indicate that such a response is likely, preferably listing a probabilistic quantification in terms of a number between 1 and 0 or as a percentage.

Turning now in more detail to the assessment operation of the evaluation unit EVAL, in one embodiment the evaluation unit EVAL operates to form respective difference images from the baseline imagery and the control imagery. Specifically, from the two image pairs, the following differences may be formed as |M1−M0| and |P1−P0|, respectively to quantify the local changes in the two indicators, pH level and metabolic activity. The order of the voxel-wise subtraction "−" is immaterial as indicated by the absolute value operator |*|.

Each voxel in the difference imagery now represents the change in extracellular pH level and metabolic activity, respectively. In one embodiment, the assessment comprises thresholding, one for the pH level factor and one for the metabolic activity factor, to compare the difference values against respective thresholds. As to establishing the indication, in one embodiment, if both the pH level change and the metabolic activity change exceed the respective thresholds this will indicate that, for at least the considered location, there is response (in particular, pseudo-progression) to the cancer therapy. However, this is one exemplary strategy for establishing the desired indication for therapy monitoring in terms of thresholding, and more strategies will be discussed further below at table 1.

In order to formulate a more robust assessment and to establish more reliable indications on responsiveness or non-responsiveness it is preferable not to rely on solely a single voxel position although this may still be done in some exceptional cases. In a preferred embodiment then, the assessment in pH level and metabolic activity changes as described above are assessed for a plurality (in particular all) of voxels in the segmented region that corresponds to the cancer lesion ROI.

In one embodiment, only voxels inside the cancer lesion segmentation are considered whilst other voxels outside the ROI are disregarded. In yet another embodiment a border margin is defined at the edge and within the ROI segmentation and it is only voxels within this margin that are taken into consideration at the described threshold based valuation as the response (if any) is likely to materialize in the border region first as observed by Applicant. In yet other embodiments, the border margin at the edge outside the ROI is established at a suitable width and only voxels with this outer margin are considered for the above described threshold based evaluation. In yet a third embodiment, the margin is partly inside and partly outside the segmentation edge.

As an alternative or in addition to the above described "dual"-thresholding with respect to difference values in pH level and metabolic activity, for each voxel a ratio is formed from the respective pH level change and the metabolic activity change as per the difference images. To each voxel then there is associated a respective ratio pH/ma (or its inverse,) where "pH" is the local pH change and "ma" is the local metabolism change. It is these ratios that are then compared for each voxel against a single threshold instead of two thresholds. An increased ratio of pH/ma has been found to be an indication for responsiveness. Again, as described above for the dual thresholding, these ratios may be considered for the assessment only inside the segmented cancer lesion ROI or in the respective border portion thereof. Alternatively, ratios for relative changes can be used as (P1−P0)/P0 and/or (M1−M0)/M0, respectively.

As a further alternative, the ratios are formed first and then the differences are taken to assess the changes. Specifically, difference images are formed from voxelwise ratio imagery of the base line and control imagery as per |P1/M1−P0/M0 or (P1−P0)/P0/(M1−M0)/M0|, where "/" indicates voxelwise division.

In all the above embodiments, although the whole of the image may be assessed voxelwise as above described this will likely increase computation time and it is preferable to restrict the assessment to the pixels in or around the segmented cancer lesion location.

In all the above threshold based embodiments, image noise is likely to corrupt the image information as recorded in the input imagery. It is therefore preferably to factor image noise into the thresholding to make the computerized assessment more robust. For instance, changes within a noise-margin $\Delta$ will be interpreted as mere noise induced fluctuations rather than a true change, and hence will be disregarded. In other words, the thresholds TR are additive and comprise, respectively, a part that represents the true change c and a part that represents noise margin $\Delta$: TR=c+$\Delta$. Alternatively or in addition, the input imagery is passed through a noise-filter-stage (not shown) to eliminate or at least reduce noise contributions by smoothing or other schemes. In case of filtering, the threshold may not need to be modified with $\Delta$ as described in the previous sentence.

As an alternative or extension of all the above, the local changes in pH level and metabolism may be combined arithmetically into expressions other than ratios, such as into weighted sums or other arithmetic combinations to so formulate different metrics for response assessment. For instance, the metabolic activity changes (relative or absolute) may be formulated based on SUVmax or other metrics.

Turning now in more detail to the operation of establishing the indicators for therapy monitoring, reference is now made to the following table (TABLE 1) where "+" indicates an increase in the respective channel, pH or metabolism, "−" indicates a decrease and "0" indicates no change (it is being understood that noise level has been factored in by the above mentioned noise margin $\Delta$ or the imagery has been noise filtered):

TABLE 1

| Metabolic (FDG) | pH (CEST) | Conclusion |
| --- | --- | --- |
| + | + | Pseudo-progression (response) |
| + | 0 | Inconclusive, most likely progression |
| + | − | Tumor progression |
| 0 | + | Inconclusive, most likely response |
| 0 | 0 | Stable tumor |
| 0 | − | Tumor progression |
| − | + | Regression (response) |
| − | 0 | Inconclusive, most likely response |
| − | − | Inconclusive |

In the above table, the metabolic assessment is based on PET/CT (18F-FDG) imagery and the extracellular pH is based on imagery acquired by MRI (CEST).

In words, the evaluator EVAL as envisaged herein is configured to establish and to distinguish any one, or a plurality (in particular all) of the following indications:
i. If the FDG signal increases over time while the pH value decreases over time, this indicates progression of the tumor.
ii. If the FDG signal increases over time and the pH value increase over time, this indicates a pseudo-progression of the tumor.
iii. If the FDG signal increases over time and the pH value is stable over time, this indicates that metabolic assessment is not conclusive.
iv. If the FDG signal is stable over time while the pH value is also stable over time, this indicates a stable tumor.
v. If the FDG signal is stable over time while the pH value decreases over time, this indicates progression of the tumor.
vi. If the FDG signal is stable over time while the pH value increases over time, this indicates that metabolic assessment is not conclusive.

vii. If the FDG signal decreases over time while the pH value is also stable over time, this indicates that metabolic assessment is not conclusive.

viii. if the FDG signal decreases over time while the pH value increases over time, this indicates that the tumor is regressing.

ix. if the FDG signal decreases over time while the pH value decreases over time, this indicates that metabolic assessment is not conclusive.

The above table may be implemented as a look-up table in the evaluator EVAL.

It will be appreciated that the proposed system is configured to distinguish progression from pseudo-progression of the lesion/tumor, as per the first and third rows in the table (and items i) and ii)). This particular discriminative capability is advantageous in particular for immunotherapy monitoring. More specifically, relative local changes in metabolic activity are compared to relative local changes in pH. In this way it is attempted to distinguish metabolic activity of tumor cells from that of immune cells and in this way to distinguish so-called pseudo- from real progression of a lesion. Constant or increased metabolic activity at increased pH (lower acidity) is interpreted as signature for response to therapy, while increased activity at constant or decreased pH is indicative of real progression.

The above indications in the table and how they are formulated i)-ix) are of equal application to imaging modalities other than 18-FDG-PET and CEST-MR.

As an alternative to the above described voxelwise assessments in terms of thresholds and metrics that may need to be learned from experience, machine learning can be used instead to examine the distributions of pH levels changes and metabolism activity changes across the input imagery to so establish patterns for responsive therapies.

To this end, historic outcome data from hospital information systems HIS collected over time of patients who underwent the same or similar cancer therapy may be used to train a suitable machine learning algorithm. The outcome training image set is naturally labeled for each patient by the outcome of the therapy, as it is already known which image in the training set corresponds to a response or non-response pattern.

In one embodiment, a neural network ("NN") may be used with two output nodes that represent respectively responsive and non-responsiveness to the immunotherapy, or a third node for inconclusiveness. Additional output nodes may be added, as per any group of indications/conclusions from the third column in the above table. The input layer nodes correspond to the size of the difference imagery for the changes in pH level and metabolic activity. There may be more than one hidden layer (eg 3 or 4) as is done in deep learning architectures. The NN can then be trained with the outcome imagery as a labeled training set to learn the relationship between i) the pH level change and metabolic activity change distributions and ii) the desired indications/conclusions such as response or non-response to a given type of cancer therapy of combinations of different types of cancer therapies. The network may be trained by suitable backward/forward algorithms as described elsewhere.

Once suitably trained, given input imagery for pH level and metabolic activity changes (e.g. in form of difference images derived from control imagery and base line imagery) may then be input into the NN and forward-propagated through the NN to directly establish the indication by examining the counts at the output nodes. However, NNs are not the only machine learning algorithms that may be used but others, such as support vector machines (SVM), regression or other statistical schemes may be used instead or in combination.

Hypoxic regions are hostile for immune effector cells. So it can be beneficial to add hypoxia marker-based imaging to complement the information from the pH level and metabolic imaging. In hypoxic regions the metabolic rate is mainly attributed to tumor cells alone. Response can lead to a reduction of the size and/or number of hypoxic regions in the lesions. One suitable imaging modality for hypoxia imaging is MR spectroscopy/MR spectroscopic imaging of 19F. This is because tumor cells cause an increased proton (H+) production, and this coupled with incomplete vascularization and poor extracellular clearance creates a hypoxic environment. Imaging for hypoxia may be particularly useful when the combined pH level and metabolism activity changes based approach as proposed herein is inconclusive.

Figure 2:
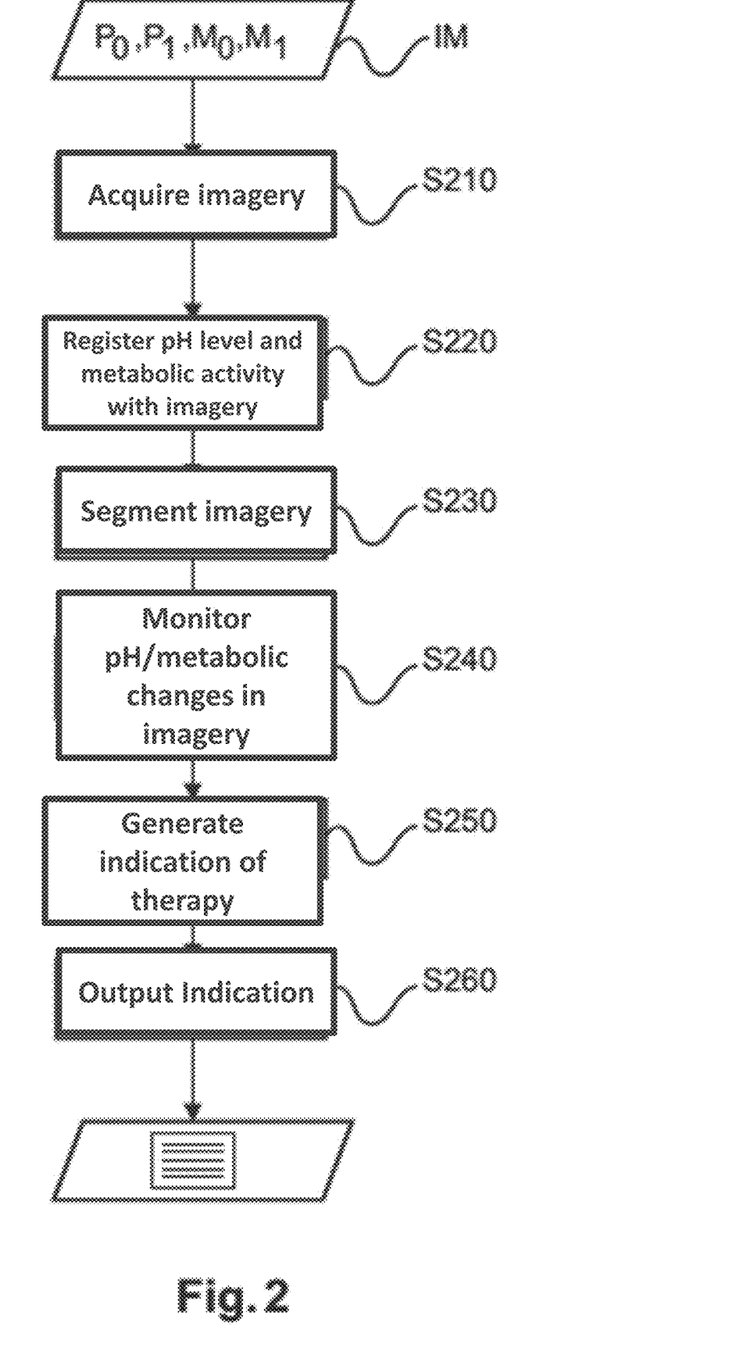
FIG. 2 shows a flow chart of a method for monitoring cancer therapy response.

Reference is now made to FIG. 2, which shows a flow chart of a method for assessing immunotherapy response. It will be understood that the following method steps may also be understood as a teaching in their own right. The computer-implemented method as proposed herein includes the following steps.

At step S210, base line imagery and control imagery is acquired of a subject that has undergone or is undergoing cancer therapy, such as immunotherapy. The base line imagery is acquired before starting the immunotherapy whilst the control imagery is acquired during or after the therapy administration. The input imagery is sensitive to extracellular pH levels and metabolic activity. In one embodiment this can be achieved by used MRI imaging for pH levels and PET imaging to capture metabolic activity, but other imaging modality combinations are also envisaged. The imagery as supplied by the modalities may need to be converted into suitable quantities such as in PET, where the radioactive intensities as recorded in the native PET image are converted into SUV or SUVmax for better comparison. In addition to functional imagery for metabolic activity and pH, morphological imaging modalities such as CT or radiography may be used to capture the spatial characteristics of the lesion. This can be preferably done by using tandem CT-PET imagers. Instead of PET, SPECT may be used herein.

At optional step S220, the pH level sensitive base line and control imagery is registered and so are the metabolic activity sensitive base line and control imagery. If the imagery is already natively registered, this step may not be necessary.

At optional step S230, a segmentation is carried out on the input imagery to segment for the cancerous lesion. The order of steps S220 and S230 may be reversed, so as to segment the imagery first and then use the segmented portions as a clue when performing the registration.

Smart segmentation schemes are also envisaged herein that provide not only a global ROI segmentation but also a refinement into sub-regions within the ROI. The steps of segmentation and registration may also be merged into a single algorithm.

In each embodiment, the segmentation is preferably configured to account for changes in size/volume of the ROI across the respective base line and control imagery. This is useful as the tumor ROI may change in size during the treatment. Segmentation schemes envisaged herein include: elastic or non-elastic, model based or not, optical flow based, and others, singly or in combination.

At step S240, changes over time in pH level and metabolic activity is then assessed using image values in the input imagery. This can be done as described by forming respective difference imagery by voxelwise subtraction based on the pH level sensitive base line imagery and the control imagery on the one hand and on the metabolic activity sensitive base line and control imagery, on the other hand. Each voxel value in the difference imagery corresponds to changes of pH level or metabolic activity, respectively. The so obtained difference values may be compared against thresholds. In addition or alternatively, ratios may be formed of pH level changes over metabolic activity changes and these ratios are then compared against a threshold. As a further alternative, the difference images are formed from voxelwise ratio imagery of the base line and control imagery as per |P1/M1−P0/M0|, where "/" indicates voxelwise division.

Instead of assessing voxelwisely, the assessment may be coarsened into chunks such as sub-ROI chunks of the whole of the ROI. The voxel-wise assessment may then be integrated or summed or otherwise combined into a respective single score or metric value for the whole of the considered ROI or sub-ROI. All of the below or above that is described herein for voxelwise processing, is hence of equal application for coarser processing based on chunks (that is, sub-sets of voxels) such as the mentioned ROIs or sub-ROIs.

At step S250, after comparing the difference values or ratios against a set of suitable thresholds or by computing other suitable metrics based on the difference (absolute or relative) values or ratios, an indication in relation to the applied cancer therapy may be established, such as responsiveness or non-responsiveness or inconclusiveness. The indication may be refined into any or more of the (sub-) indications as per the third column in the table above.

In one embodiment the segmented ROI as per step S230 comprises the whole lesion, but this may be refined by sub-segmentation into areas of similar metabolic activity, and/or into a core and a peripheral or boundary region, or based on CT or MRI morphological information. The assessment step S240 is then carried out for each sub-segment. The overall conclusion/indication at step S250 can be derived by forming (weighted) averages over the whole tumor lesion or by formulating different metrics. In immunotherapy, one may expect an earlier response at the border region of the tumor, therefore the border region may deserve more attention in the assessment than the core region.

In one embodiment, each voxel is treated separately as described above, with each voxel having its own assessment and indication. The overall conclusion/indication for the whole ROI (or sub-ROIs) may then be formed by majority voting across all considered voxels or by taking a simple or weighted average of all assessments from which the overall indication is then derived as per the table above. Assessments for voxels from the border region (or from any other specified region) may be attract higher weights in the averaging. Border region voxel may also attract more votes in a majority vote. Preferably, the assessment is restricted to voxels/pixels in the segmented region only.

If morphological information is available as from base line and control CT imagery, volumetric changes may be factored into the above assessment. In particular, corrections for changes in the lesion volume may be necessary. In one embodiment, a factoring-in of volume changes may be done by normalizing the above described assessment values by volume size.

As to the formulation of the indication, the change in volume of the lesion may be formulated as a separate metric or the volume change may be combined into the metabolic-activity-and-pH-level metric as discussed above.

The indication may be established as a binary indication on whether there is response or there is no response, or the indication may be formulated in probabilistic or statistical terms such as percentage value.

For example, for the segmented ROI, the percentage values of those ratios or difference values that are above the relative thresholds may be computed relative to those that are below the thresholds to so arrive at a value between zero and one which may be interpreted as a probability for therapy response.

Instead of the above threshold based approach, machine learning algorithms or statistical algorithms may be used. It will be understood that in particular in the machine learning algorithm, the above steps of assessing S240 the changes and of establishing S250 the indication, are essentially merged into one.

The indication may then be output at step S260 on a monitor device MT such as on a screen of a laptop, desk computer, smart-phone or otherwise.

The indication may be suitably color-coded or otherwise graphically rendered for instance such as "red" for no response and "blue" for response or shadings between the two, or similar.

Instead of or in addition to displaying the indication on a display device, the data may be stored on a memory MEM such as a database or may otherwise be processed.

It will be appreciated that the assessment step S240 may be repeated at multiple times (N>1) for multiple control imagery sets acquired at different times $T_1^k$ (k=1, 2, ... N). The changes of the ratios may then be plotted for each voxel over time. In principle however, the proposed method is operational for a single pair or base line and control imagery.

All of the above embodiments may be complemented, modified or extended by the following:

Instead of FDG also other direct lactate imaging can be employed. Alternative to MRI pH imaging, PET contrast agents for pH can be employed.

Systemic LDH (Lactate dehydrogenase) measurements can be used to compare with the integrated FDG activity of all lesions before and after onset of therapy.

LDH and cell counts in blood can be monitored before and during therapy to get additional information concerning the response of the patient in combination with the radiology information.

FLT (Fluorothymidine F-18)-PET can be added in order to see the proliferative activity of the tumor lesions. This is mainly interpreted as signature of progression, however, it has to be corrected for potential contributions from the proliferation of immune cells. FLT information can help in further improving the confidence in the conclusion drawn from the metabolic and pH imaging.

Very acidic tumor areas are likely to not allow a successful activity of effector cells, so their metabolic activity is expected to be low, even when recruited to the tumor.

Recruitment (more immune cells go to the tumor site) of immune cells can be also observed by adding immuno-PET imaging, for instance with radio-labeled anti-CD8 agents.

One or more features or the method as disclosed herein may be configured or implemented as/with circuitry encoded within a computer-readable medium, and/or combinations thereof. Circuitry may include discrete and/or integrated circuitry, application specific integrated circuitry (ASIC), a system-on-a-chip (SOC), and combinations thereof, a machine, a computer system, a processor and memory, a computer program.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium (in particular, but not necessarily, a non-transitory medium), such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A computerized system for monitoring cancer therapy, comprising:
    an input port for receiving two or more input images acquired of a subject, a first input image of the two or more input images recording metabolic activity based on a PET image and a second input image of the two or more input images recording extracellular pH level based on an MR image;
    a computer configured to:
    segment the two or more input images to find a lesion in the two or more input images;
    assess i) a change (ma) in metabolic activity and ii) a change (pH) in extracellular pH level in the segmented two or more images by converting image values in the two or more input images to standard uptake values (SUVs):
    form, from the SUVs, at least one ratio of pH/ma or ma/pH; and
    c in relation to the lesion or on whether the assessment is inconclusive; and
    an output interface for outputting said indication.

2. The system of claim 1, wherein the computer is configured to establish in the indication that there is response to the cancer therapy if i) there is an increase in metabolic activity and there is increase in extracellular pH level or ii) there is a decrease in metabolic activity and increase in extracellular pH level.

3. The system of claim 1, wherein the computer is configured to establish in the indication whether the response is a pseudo-progression or a real progression.

4. The system of claim 1, wherein the computer includes an image segmenter to segment the two or more images for a region of interest (ROI), wherein the assessment of the changes of the metabolic activity and the extracellular pH level is based on image values in said ROI.

5. The system of claim 1, wherein the assessment of the changes of the metabolic activity and the extracellular pH level is based on image values in a border portion of the ROI.

6. A non-transitory computer readable medium storing instructions executable by at least one processor to perform a computer-implemented method to monitor cancer therapy, the method comprising:
    receiving two or more input images acquired of a subject, a first input image of the two or more input images recording metabolic activity based on a PET image and a second input image of the two or more input images recording extracellular pH level based on an MR image;
    segmenting the two or more input images to find a lesion in the two or more input images;
    assessing i) a change (ma) in metabolic activity and ii) a change (pH) in extracellular pH level in the segmented two or more images by converting image values in the two or more input images to standard uptake values (SUVs):

forming, from the SUVs, at least one ratio of pH/ma or ma/pH; and establishing, based on the at least one ratio of pH/ma or ma/pH, an indication on whether or not there is a response to a cancer therapy in relation to the lesion or on whether the assessment is inconclusive; and outputting said indication.

7. The non-transitory computer readable medium as per claim 6, wherein the establishing includes establishing in the indication that there is response to the cancer therapy, if i) there is an increase in metabolic activity and there is increase in extracellular pH level or ii) there is a decrease in metabolic activity and an increase in extracellular pH level.

8. The non-transitory computer readable medium as per claim 6, wherein the established indication is capable of distinguishing between a pseudo-progression and a real progression.

9. The non-transitory computer readable medium as per claim 6 wherein the establishing includes applying machine learning to the images.

10. A system for monitoring cancer therapy, comprising:

a positron emission tomography (PET) imager configured to acquire a PET image of a subject recording metabolic activity;

a magnetic resonance imaging (MRI) imager configured to acquire an MRI image of the subject recording extracellular pH level; and a computer configured to:

assess a change (ma) over time in metabolic activity using the PET image and a change (pH) over time in extracellular pH level using the MRI image;

establish, based on the assessment, an indication on whether or not there is a response to a cancer therapy in relation to a lesion of the subject or on whether the assessment is inconclusive based on computing at least one ratio of pH/ma or ma/pH; and output said indication.

* * * * *